United States Patent [19]

Bettarini et al.

[11] 4,356,329

[45] Oct. 26, 1982

[54] HYDROQUINONE ETHERS HAVING JUVENILE HORMONE ACTIVITY

[75] Inventors: Franco Bettarini, Novara; Pietro Massardo, Milan; Paolo Piccardi, Milan; Angelo Longoni, Milan, all of Italy

[73] Assignee: Montedison S.p.A., Milan, Italy

[21] Appl. No.: 198,488

[22] Filed: Oct. 20, 1980

Related U.S. Application Data

[63] Continuation-in-part of Ser. No. 50,335, Jun. 20, 1979, abandoned.

[30] Foreign Application Priority Data

Jun. 21, 1978 [IT] Italy ................................ 24794 A/78
Mar. 5, 1979 [IT] Italy ................................ 20734 A/79

[51] Int. Cl.$^3$ ........................................... C07C 43/215
[52] U.S. Cl. ................................... 568/637; 568/649; 424/341
[58] Field of Search ................................. 568/637, 649

[56] References Cited

U.S. PATENT DOCUMENTS 3,322,813 5/1967 Seki et al. ...................... 568/649 X
3,379,755 4/1968 Schultz ........................... 568/649 X
3,816,541 6/1974 Mihailovski et al. ............... 568/649
4,061,683 12/1977 Karrer ........................... 568/637 X
4,126,623 11/1978 Piccardi et al. ................. 260/340.5 R
4,141,921 2/1979 Karrer ........................... 568/637
4,153,731 5/1979 Karrer ........................... 568/637 X

FOREIGN PATENT DOCUMENTS 2528314 1/1976 Fed. Rep. of Germany .

*Primary Examiner*—Bernard Helfin

[57] ABSTRACT

There are disclosed two hydroquinone diethers having at least one acetylenic and halogen-substituted chain and exhibiting juvenile hormone and acaricide activity and which show unexpected activity on *Tenebrio molitor* and *Tribolium confusum*.

The two hydroquinone ethers are obtained by:
(a) reacting one mole of hydroquinone alkali metal salt with two moles of 1,5-dichloropent-4-yne, or equimolar quantities of an alkali metal salt of 4-phenoxy-phenol with 1,5-dichlorpent-4-yne; or
(b) by reacting the hydroquinone alkali metal salt or the 4-phenoxy-phenol alkali metal salt with the indicated quantities of 1,1,1,5-tetrachloropentane and then dehydrohalogenating the condensation product with alkali metal carbonates or hydroxides in dimethylsulphoxide.

5 Claims, No Drawings

HYDROQUINONE ETHERS HAVING JUVENILE HORMONE ACTIVITY

This is a continuation-in-part of our application Ser. No. 50,335 filed June 20, 1979 and now abandoned.

THE PRIOR ART

U.S. Pat. No. 4,061,683 describes compounds of general formula:

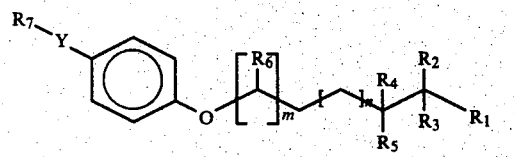

in which
R$_1$ is hydrogen, halogen, alkyl, vinyl or ethynyl;
R$_2$ is hydrogen, halogen, methyl or ethyl;
R$_3$ is hydrogen, methyl or alkoxyl;
R$_4$ is hydrogen, halogen or methyl;
R$_5$ is hydrogen or R$_3$ and R$_5$ form a carbon-carbon bond or an oxygen bridge;
R$_6$ is hydrogen or methyl;
R$_7$ is cyclohexyl or a variously substituted phenyl group;
Y is either a methylene or an oxymethylene bridge; and
m and n are either 0 or 1,
as showing insecticide activity against Orthoptera, Isoptera, Hemiptera, Coleoptera, Lepidoptera, Diptera and Acarina.

Among other compounds (col. 17, No. 30 and col. 19, No. 46) the compound

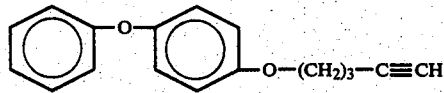

is disclosed.

In U.S. Pat. No. 4,153,731, there are disclosed compounds of the general formula:

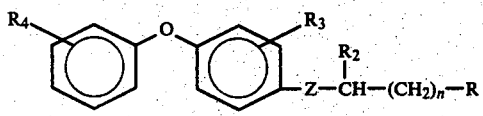

in which
n is 0 or 1;
Z represents oxygen or sulphur;
R$_1$ represents a substituted phenyl group;
R$_2$ represents hydrogen, methyl or ethyl; and
R$_3$ and R$_4$ each represents hydrogen, methyl, ethyl, methoxy, ethoxy, nitro or halogen.

Such compounds are described as able to control a large number of insects, including Acarididae, Tenebrionidae, etc.

U.S. Pat. No. 4,000,312 and U.S. Pat. No. 4,140,794 describe aliphatic compounds having juvenile hormonal activity and a dichloro- or trichloro-substituted end vinyl group bound to a phenyl or substituted phenyl group. Among them, only those having a trichloromethyl terminal group exhibit acaricidal activity.

THE PRESENT INVENTION

One object of the present invention is to provide two new hydroquinone diethers having an acetylenic and halosubstituted terminal group which exhibit both juvenile hormonal and acaricidal activity and unexpectedly high activity against *Tenebrio molitor, Aedes Aegypti and Musca domestica.*

Another object of the invention is to provide an improved method for fighting infestations due to noxious insects.

Still another object of the invention is that of providing two methods for obtaining such compounds.

These and other objects are achieved by this invention which provides two new hydroquinone diethers of formulae:

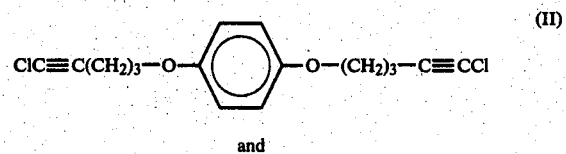

and

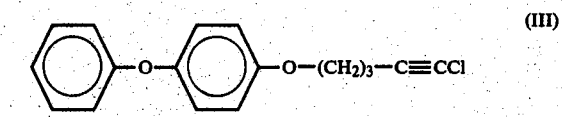

and which, besides exhibiting acaricide activity, exhibit a complete activity on *Tribolium confusum*, at 2 p.p.m., *Aedes aegypti* at 0.02 p.p.m.; on *Musca domestica* at 20 p.p.m.; and on *Tenebrio* at doses of 0.02 γ (micrograms, 1/10$^6$ g) per insect.

The two new compounds II and III show the following $^1$Hnmr spectrum (in CDCl$_3$).

| | |
|---|---|
| 1,4-di-(5-chloro-4-pentinyloxy)-benzene: | δ = 1.7–2.7 (8H, complex); |
| ClC≡C—(CH$_2$)$_3$—O—⟨O⟩—O—(CH$_2$)$_3$—C≡CCl | 3.97 (4H, t); 6.8 (4H, s); |
| 1-(5-chloro-4-pentinyloxy)-4-phenyloxy-benzene: | δ = 1.6–2.6 (4H complex); |
| ⟨O⟩—O—⟨O⟩—O—(CH$_2$)$_3$—C≡CCl | 3.9 (2H, t); 5.9 (1H, t); 6.6–7.5 (9H complex) | and may be prepared by reacting the sodium salt of hydroquinone or of phenoxy-phenol with 1,5-dichloro-1-pentine.

Instead of reacting the 1,5-dichloro-1-pentine with the hydroquinone alkali metal salt or with the alkali metal salt of phenoxy-phenol, the hydroquinone alkali metal salt or the alkali metal salt of phenoxy-phenol may be reacted with 1,1,1,5-tetrachloropentane, following by dehydrohalogenation of the reaction product at temperatures of 50°–100° C., preferably at 80° C., in dimethylsulphoxide.

The activity of the compounds of this invention, in comparison with the activity of the compound of formula I hereinabove, has been determined as described in Example 3, infra. The results are summarized in the following Table.

TABLE I

Comparison of the juvenile hormonal activities of compounds I, II, III

| Compound | Tribolium confusum dose 2 ppm | Anagasta kuehniella dose 20 ppm | Aedes aegypti dose 0.02 ppm | Musca domestica dose 20 ppm | Tenebrio molitor dose 0.02 $\gamma$/ins. |
|---|---|---|---|---|---|
| I | 0 | 40 | 0 | 0 | 0 |
| II | 100 | 100 | 100 | 100 | 100 |
| III | 100 | 100 | 100 | 100 | 100 |

As appears from Table I, the compounds of the present invention are far more active than compound I, the activity of which latter is recognizable only at 20 ppm on *Tribolium confusum;* at 0.2 ppm on *Aedes aegypti;* at 100 ppm on *Musca domestica* and at 0.2 $\gamma$/ins. on *Tenebrio molitor*. It is surprising that the substitution of a terminal H atom by a Cl atom can improve the hormonal juvenile activity 10 times or more.

The following examples are given to illustrate the invention in more detail and are not intended to be limiting:

EXAMPLE 1

Preparation of 1,4-di-(5-chloro-4-pentinyloxy)-benzene(II) (JH20)

In 100 ml of DMF (dimethylformamide) were dissolved 5 g of hydroquinone and 4.5 g of NaOH and the solution was stirred for 1 hour at room temperature. 14 grams of 1,5-dichloro-1-pentine were dripped into the solution and the mixture was then heated to 60° C. for 6 hours.

At the end, the reaction mixture was cooled down, poured into water and extracted with ethyl ether. The ether extract was then neutralized with diluted HCl, washed with water, anhydrified with $Na_2SO_4$, and finally concentrated. The residue was chromatographed on a silica gel colum; by eluting with ether and petroleum ether 95:5, 6 g 1,4-di(5-chloro-4-pentinyloxy)-benzene were obtained having the following characteristics:

m.p.=62° C.; $^1$Hn.m.r. spectrum (in $CDCl_3$); $\delta$=1.7–2.7 (8H, complex); 3.97 (4H, t); 6.8 (4H, s).

EXAMPLE 2

Preparation of 1-(5-chloro-4-pentinyloxy)-4-phenoxy-benzene (JH286)

Two gms of 4-phenyloxy-phenol were dissolved in 10 ml of dimethylsulphoxide and 1.6 g of milled NaOH were added to the solution. The mixture was then stirred for one hour at room temperature, after which 2.5 g. of 1,1,1,5-tetrachloropentane were dripped into the mixture. The mixture was then heated to 60° C. and kept at that temperature for 6 hours.

After 6 hours, the mixture was poured into water, then extracted with ethyl ether. The residue thus obtained, by concentration of the etheric phase, was purified on the chromatographic column as in Example 1. Thereby were obtained 2.1 g. of a compound showing the following $^1$Hn.m.r. characteristics (in $CDCl_3$): $\delta$1.7–2.6 (4H, complex); 3.97 (2H, t); 6.7–7.5 (9H, complex).

EXAMPLE 3

Tests of juvenile hormonal activity (a) *Tribolium confusum*

5 g of wheat meal were uniformly treated with an acetone solution of the product. 24 hours after the treatment, the meal or flour was infested with 22 days old larvae. Survey of the results was made about 45 days later when the insects of the witness group had completed emergence from the cocoons.

(b) *Anagasta kuehniella*

5 g of maize meal were uniformly treated with an acetone solution of the product. 24 hours after the treatment, the meal or flour was infested with 21 days old larvae. The survey of the results was made every 3–4 days starting from the first appearance of the adult insects until the end of the emergence from the cocoons in the witness group.

(c) *Aedes aegypti*

3 cc of an acetone solution of the product were added to 297 cc of tap water into which were successively transferred 25 larvae, four days old, supplying them the suitable food.

Surveyings of the results were made every 2–3 days until the end of the emergence from the cocoons in the witness group.

(d) *Musca domestica* (larvae)

250 g of artificial nutrient medium were mixed with 5 ml of an acetone solution of the product and then infested with 100 larvae, 2 days old. After 6 days, the pupae in the nutrient medium were collected and kept apart waiting for adults. The results were calculated when all the pupae of the control test (without the substances having juvenile hormonal activity) developed into adults.

(e) *Tenebrio molitor*

0–24 hours aged pupae were treated by topical application on the antepenultimate urosternite with an acetone solution of the products (2 micro liters). A survey of the results was taken after about 9 days when the insects of the witness group completed their emergence from the cocoons.

(f) Tetranychus urticae

Eggs—Bean leaves discoids were infested with acari eggs and were then treated by sprinkling on them an aqueous dispersion having a concentration of 1% of the compound under examination. The percent mortality was evaluated as 0 in the untreated leaves discoids.

Adults—Bean leaves discoids were infested with acari adults and successively treated with an aqueous dispersion of 0.1% of the product being tested. The percent mortality was valued 0 for the untreated leaves discoids.

As activity index there was adopted the percentual ratio of dead individuals, misshaped and abnormal individuals with respect to the number of treated individuals, as may be deduced from the following formula:

$$\text{activity} = \frac{(\text{dead} + \text{misshaped} + \text{abnormal individuals})}{\text{treated individuals}} \%$$

The results for hormonal juvenile activity are summarized in Table I; the activity on *Tetranychus urticae* at 1% dose is the following.

TABLE II

| Acaricidal activity on *Tetranychus urticae*, adults and eggs, of compounds I, II, III at 1% concentration | | |
|---|---|---|
| | *Tetranychus urticae* | |
| Compound | adults | eggs |
| I | 18 | 80 |
| II | 18 | 87 |
| III | 83 | 100 |

What we claim is:
1. Hydroquinone diethers selected from 1,4-di-(5-chloro-4-pentinyloxy)-benzene of formula

and 1-(5-chloro-4-pentinyloxy)-4-phenyloxybenzene of formula

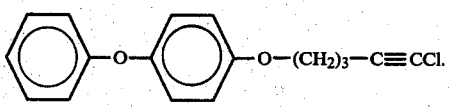

2. A hydroquinone diether according to claim 1, and being 1,4-di(5-chloro-4-pentinyloxy)-benzene.
3. A hydroquinone diether according to claim 1, and being 1-(5-chloro-4-pentinyloxy)-4-phenyloxybenzene.
4. A process for preparing 1,4-di-(5-chloro-4-pentinyloxy)-benzene of claim 1, in which a hydroquinone alkali metal salt is reacted with 1,1,1,5-tetrachloropentane, and the resulting product is dehydro halogenated with alkali carbonate or hydroxide at 50°–100° C., in dimethylsulphoxide.
5. A process for preparing 1-(5-chloro-4-pentinyloxy)-4-phenyloxybenzene of claim 1, in which a 4-phenoxy-phenol alkali metal salt is reacted with 1,1,1,5-tetrachloropentane, and the resulting product is dehydrogenated with alkali carbonate or hydroxide at 50°–100° C., in dimethylsulphoxide.

* * * * *

UNITED STATES PATENT AND TRADEMARK OFFICE
CERTIFICATE OF CORRECTION

PATENT NO. : 4,356,329

DATED : October 26, 1982

INVENTOR(S) : Franco Bettarini et al.

It is certified that error appears in the above-identified patent and that said Letters Patent is hereby corrected as shown below:

The data in the last two lines at the right side of the table in column 2, should read as follows:

---δ1.7-2.6 (4H, complex); 3.97 (2H,t); 6.7-7.5 (9H, complex)---

Signed and Sealed this

Twenty-ninth Day of January 1985

[SEAL]

Attest:

DONALD J. QUIGG

Attesting Officer     Acting Commissioner of Patents and Trademarks